US009326735B2

(12) United States Patent
Muhlsteff

(10) Patent No.: US 9,326,735 B2
(45) Date of Patent: May 3, 2016

(54) METHOD AND APPARATUS FOR MONITORING CARDIAC OUTPUT OF A PATIENT IN A HOME ENVIRONMENT

(71) Applicant: KONINKLIJKE PHILIPS N.V., Eindhoven (NL)

(72) Inventor: Jens Muhlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/399,759

(22) PCT Filed: Apr. 23, 2013

(86) PCT No.: PCT/IB2013/053198
§ 371 (c)(1),
(2) Date: Nov. 7, 2014

(87) PCT Pub. No.: WO2013/171599
PCT Pub. Date: Nov. 21, 2013

(65) Prior Publication Data
US 2015/0126820 A1     May 7, 2015

Related U.S. Application Data

(60) Provisional application No. 61/646,941, filed on May 15, 2012.

(51) Int. Cl.
*A61B 5/02*     (2006.01)
*A61B 5/00*     (2006.01)
(Continued)

(52) U.S. Cl.
CPC ............. *A61B 5/7278* (2013.01); *A61B 5/0205* (2013.01); *A61B 5/029* (2013.01);
(Continued)

(58) Field of Classification Search
CPC ...... A61B 5/029; A61B 5/0295; A61B 8/065; A61B 8/06; A61B 5/7278; A61B 5/0205; A61B 5/0261

USPC .......................................... 600/526, 508, 509
See application file for complete search history.

(56) References Cited

U.S. PATENT DOCUMENTS 6,485,431 B1   11/2002   Campbell
6,561,986 B2    5/2003   Baura et al.
(Continued)

FOREIGN PATENT DOCUMENTS

EP      0969897 B1    8/2010
WO      0047110 A1    8/2000

OTHER PUBLICATIONS

Muehlsteff, J. et al. Continuous Cuff-less Blood Pressure Monitoring based on the Pulse Arrival Time Approach: The Impact of Posture. 2008. 30th Annual International IEEE EMBS Conference. p. 1691-1694.*

(Continued)

*Primary Examiner* — Christopher D Koharski
*Assistant Examiner* — Michael Carey

(57) ABSTRACT

There is provided a method of determining a measure of the cardiac output, CO, of a patient, the method comprising obtaining measurements of one or more physiological characteristics of the patient, the physiological characteristics including at least the heart rate, HR, of the patient, the systolic blood pressure, S, of the patient and the diastolic blood pressure, D, of the patient; and processing the measurements to determine a measure of the cardiac output of the patient; wherein the measure of the cardiac output of the patient is derived using the relationship $$CO = K_1\left(HR\frac{S-D}{S+D}\right), CO = K_2 HR(S-D)(PTT)^2, \text{ and/or}$$

$$CO = K_2 HR(S-D)(PAT-PEP)^2$$

where $K_1$ and $K_2$ are patient-specific calibration factors, PAT is the pulse arrival time, PEP is the pre-ejection period and PTT is the pulse transit time, the time taken for a pulse wave to travel between two points in the body of the patient.

14 Claims, 4 Drawing Sheets

(51) Int. Cl.
A61B 5/029 (2006.01)
A61B 5/0205 (2006.01)
A61B 5/026 (2006.01)
A61B 5/0402 (2006.01)
A61B 5/11 (2006.01)
A61B 7/04 (2006.01)
A61B 7/00 (2006.01)
A61B 5/024 (2006.01)
A61B 5/021 (2006.01)

(52) U.S. Cl.
CPC ............ *A61B 5/0261* (2013.01); *A61B 5/0402* (2013.01); *A61B 5/1116* (2013.01); *A61B 5/486* (2013.01); *A61B 5/7225* (2013.01); *A61B 5/7246* (2013.01); *A61B 5/7285* (2013.01); *A61B 5/742* (2013.01); *A61B 5/7475* (2013.01); *A61B 7/045* (2013.01); *A61B 5/021* (2013.01); *A61B 5/02007* (2013.01); *A61B 5/02416* (2013.01); *A61B 7/006* (2013.01); *A61B 2505/07* (2013.01)

(56) References Cited

U.S. PATENT DOCUMENTS 7,670,295 B2 3/2010 Sackner et al.
2005/0222514 A1* 10/2005 Sugo .................. A61B 5/029 600/526
2011/0066042 A1 3/2011 Pandia et al.

OTHER PUBLICATIONS

Aubert et al, Non-Invasive Cuff-Less Measurements of the Arterial Blood Pressure: What Does Pulse-Transit-Time Tell US All About? Proc. ESGO, Jena, Germany, May 2006, pp. 211-214.
Carvalho et al, "Robust Characteristic Points for ICG: Definition and Comparative Analysis", Conference: Biosignals 2011, Proceedings of the International Conference on Bio-Inspired Systems and Signal Processing, Jan. 2011, pp. 1-9.
Morren et al, "Fall Prediction Based on Vital Sign Monitoring", Philps Report PR-TN2008-00411, 2008, pp. 1-53.
Muehlsteff et al, "Cuffless Estimation of Systolic Blood Pressure for Short Effort Bicycle Test: The Prominent Role of the Pre-Ejection Period", Proceeding of the 28th IEEE EMBS Annual International Conference New York, NY, 2006, pp. 5088-5092.
Muehlsteff et al, "Continuous Cuff-Less Blood Pressure Monitoring Based on the Pulse Arrival Time Approach: The Impact of Posture", 30th Annual International IEEE EMBS Conference, Canada, 2008, pp. 1691-1694.
Carvalho et al, "Comparison of Systolic Time Interval Measurement Modalities for Portable Devices", 32nd Annual International Conference of the IEEE EMBS, Argentina, 2010, pp. 606-609.

* cited by examiner

METHOD AND APPARATUS FOR MONITORING CARDIAC OUTPUT OF A PATIENT IN A HOME ENVIRONMENT

CROSS-REFERENCE TO PRIOR APPLICATIONS

This application is the U.S. National Phase application under 35 U.S.C. §371 of International Application Ser. No. PCT/IB2013/053198, filed on Apr. 23, 2013, which claims the benefit of U.S. Application Ser. No. 61/646,941, filed on May 15, 2012. These applications are hereby incorporated by reference herein.

TECHNICAL FIELD OF THE INVENTION

The invention relates to a method and apparatus for monitoring the health of a patient in a home environment, and in particular relates to a method and apparatus for monitoring the cardiac output (CO) of a patient in a home environment.

BACKGROUND TO THE INVENTION

The management of Congestive Heart Failure (CHF) patients is currently based on easy-to-acquire measurements such as heart rate (HR), weight and blood pressure (BP). However, these measurements respond late to changes of the patient health status and provide limited information to personalize and adapt medication therapy.

Cardiac output (CO)—the volume of blood pumped by the left ventricle of the heart per minute—and systemic vascular resistance (SVR)—the resistance of the circulatory system to the pumping of blood through it—are both established clinical measures that respond reasonably early to changes of the health of a patient. Stroke volume (SV)—the volume of blood pumped by a ventricle per heart beat—is another useful measure of the health of the cardiovascular system of a patient. However, it is currently only possible to make reliable measurements of CO, SVR and SV in a clinical environment (such as a hospital). In particular, echocardiography currently the clinical 'gold standard' for non-invasive CO measurements, requires expensive, bulky equipment and well-trained operators. Impedance cardiography (ICG) has been considered as one of the most promising techniques for use in a home environment, but current implementations do not provide accurate CO readings for patients with CHF.

It is therefore desirable to provide ways to easily and reliably determine cardiac output and the other measures indicated above for a patient in unsupervised settings, such as at home, for use in monitoring the health of the cardiovascular system of the patient and adapting the dosage or type of medication prescribed to the patient to improve the management of CHF and reduce side effects of the medication.

SUMMARY OF THE INVENTION

According to a first aspect of the invention, there is provided a method of determining a measure of the cardiac output, CO, of a patient, the method comprising obtaining measurements of one or more physiological characteristics of the patient, the physiological characteristics including at least the heart rate, HR, of the patient, the systolic blood pressure, S, of the patient and the diastolic blood pressure, D, of the patient; and processing the measurements to determine a measure of the cardiac output of the patient; wherein the measure of the cardiac output of the patient is derived using the relationship $$CO = K_1 \left( HR \frac{S-D}{S+D} \right),$$

$$CO = K_2 HR(S-D)(PTT)^2,$$

and/or $$CO = K_2 HR(S-D)(PAT-PEP)^2,$$

where $K_1$ and $K_2$ are patient-specific calibration factors, PAT is the pulse arrival time, PEP is the pre-ejection period and PTT is the pulse transit time, the time taken for a pulse wave to travel between two points in the body of the patient.

In some embodiments, where absolute measures of the cardiac output are required, $K_1$ and/or $K_2$ are determined from a reference measurement of the cardiac output of the patient.

In alternative embodiments, the measure of the cardiac output of the patient is a measure of the change in the cardiac output from an earlier cardiac output measurement or a reference measurement for cardiac output, and the measure of the change in the cardiac output is given by $$\frac{CO}{CO_{ref}} = \left( HR \frac{S-D}{S+D} \right) \bigg/ \left( HR \frac{S-D}{S+D} \right)_{ref},$$

$$\frac{CO}{CO_{ref}} = (HR(S-D)PTT^2)/(HR(S-D)PTT^2)_{ref},$$

and/or $$\frac{CO}{CO_{ref}} = (HR(S-D)(PAT-PEP)^2)/(HR(S-D)(PAT-PEP)^2)_{ref}$$

where $(\ldots)_{ref}$ denotes the earlier cardiac output measurement or the reference measurement for cardiac output.

In some embodiments, the step of obtaining measurements comprises obtaining an electrocardiogram signal, a photoplethysmogram signal, and at least one of heart sounds and an impedance cardiogram signal; and wherein the step of processing comprises processing the electrocardiogram signal and photoplethysmogram signal to determine the pulse arrival time, and processing the at least one of the heart sounds or the impedance cardiogram signal and the electrocardiogram signal to determine the pre-ejection period.

In preferred embodiments, the method further comprises the steps of comparing the measure of the cardiac output of the patient or measure of the change in the cardiac output of the patient to one or more threshold values; and providing an output indicating the result of the step of comparing.

In some embodiments, the method further comprises the steps of obtaining measurements of acceleration acting on the patient during the measurement of the physiological characteristics of the patient; processing the measurements of acceleration to determine the posture of the patient; comparing the determined posture of the patient to a predetermined posture for the patient; and providing feedback to the patient regarding their posture if the determined posture is not the same or sufficiently close to the predetermined posture.

Preferably, the predetermined posture corresponds to the posture of the patient during a previous set of measurements of the physiological characteristics of the patient. In this way, it can be ensured that differences in measurements of the one or more physiological characteristics are not caused by changes in posture of the patient.

In preferred embodiments, the method further comprises the step of processing the measurements to determine a measure of the systemic vascular resistance, SVR, of the patient from the measure of the cardiac output of the patient using the relationship SVR=MAP/CO where MAP is the mean arterial blood pressure and is given by MAP=S/3+2D/3.

According to a second aspect of the invention, there is provided a computer program product comprising computer readable code that, when executed by a suitable computer or processor, is configured to cause the computer or processor to perform the method described above.

According to a third aspect of the invention, there is provided an apparatus for use in monitoring the cardiac output, CO, of a patient, the apparatus comprising processing means configured to receive measurements of one or more physiological characteristics of the patient, the physiological characteristics including at least the heart rate, HR, of the patient, the systolic blood pressure, S, of the patient and the diastolic blood pressure, D, of the patient; and process the measurements to determine a measure of the cardiac output of the patient; wherein the measure of the cardiac output of the patient is derived using the relationship $$CO = K_1\left(HR\frac{S-D}{S+D}\right),$$
$$CO = K_2 HR(S-D)(PTT)^2,$$
and/or
$$CO = K_2 HR(S-D)(PAT-PEP)^2$$

where $K_1$ and $K_2$ are patient-specific calibration factors, PAT is the pulse arrival time, PEP is the pre-ejection period and PTT is the pulse transit time, the time taken for a pulse wave to travel between two points in the body of the patient.

In some embodiments, where absolute measures of the cardiac output are required, the processing means is configured to obtain $K_1$ and/or $K_2$ from a reference measurement of the cardiac output of the patient.

In alternative embodiments, the measure of the cardiac output of the patient determined by the processing means is a measure of the change in the cardiac output from an earlier cardiac output measurement or a reference measurement for cardiac output, and the processing means is configured to process the measurements to determine the measure of the change in the cardiac output using $$\frac{CO}{CO_{ref}} = \left(HR\frac{S-D}{S+D}\right)\bigg/\left(HR\frac{S-D}{S+D}\right)_{ref},$$
$$\frac{CO}{CO_{ref}} = (HR(S-D)PTT^2)/(HR(S-D)PTT^2)_{ref},$$
and/or
$$\frac{CO}{CO_{ref}} = (HR(S-D)(PAT-PEP)^2)/(HR(S-D)(PAT-PEP)^2)_{ref}$$

where $(\ldots)_{ref}$ denotes the earlier cardiac output measurement or the reference measurement for cardiac output.

In some embodiments, the processing means is further configured to compare the measure of the cardiac output of the patient or measure of the change in the cardiac output of the patient to one or more threshold values; and provide an output indicating the result of the comparison.

In some embodiments, the apparatus further comprises any one or more of the following physiological characteristic sensors: a blood pressure monitor, a heart rate sensor, an electrocardiogram sensor, a photoplethysmogram sensor, an impedance cardiogram sensor and one or more microphones.

In preferred embodiments, the one or more physiological characteristic sensors are integrated into an item of clothing to be worn by the patient.

In particular embodiments, the processing means is configured to receive signals from an electrocardiogram, a photoplethysmogram, and at least one of a microphone that records heart sounds and an impedance cardiogram; and the processing means is configured to process the electrocardiogram signal and photoplethysmogram signal to determine the pulse arrival time, and to process the at least one of the heart sounds or the impedance cardiogram signal and the electrocardiogram signal to determine the pre-ejection period.

In some embodiments, the processing means is further configured to receive measurements of the acceleration acting on the patient and to process the measurements of the acceleration to determine the posture of the patient.

The processing means can be further configured to compare the determined posture of the patient to a predetermined posture for the patient; and provide feedback to the patient regarding their posture if the determined posture is not the same or sufficiently close to the predetermined posture. Preferably, the predetermined posture corresponds to the posture of the patient during a previous set of measurements of the physiological characteristics of the patient. In this way, it can be ensured that differences in measurements of the one or more physiological characteristics are not caused by changes in posture of the patient.

In preferred embodiments, the processing means is further configured to process the measurements to determine a measure of the systemic vascular resistance, SVR, of the patient from the measure of the cardiac output of the patient using the relationship SVR=MAP/CO where MAP is the mean arterial blood pressure and is given by MAP=S/3+2D/3.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
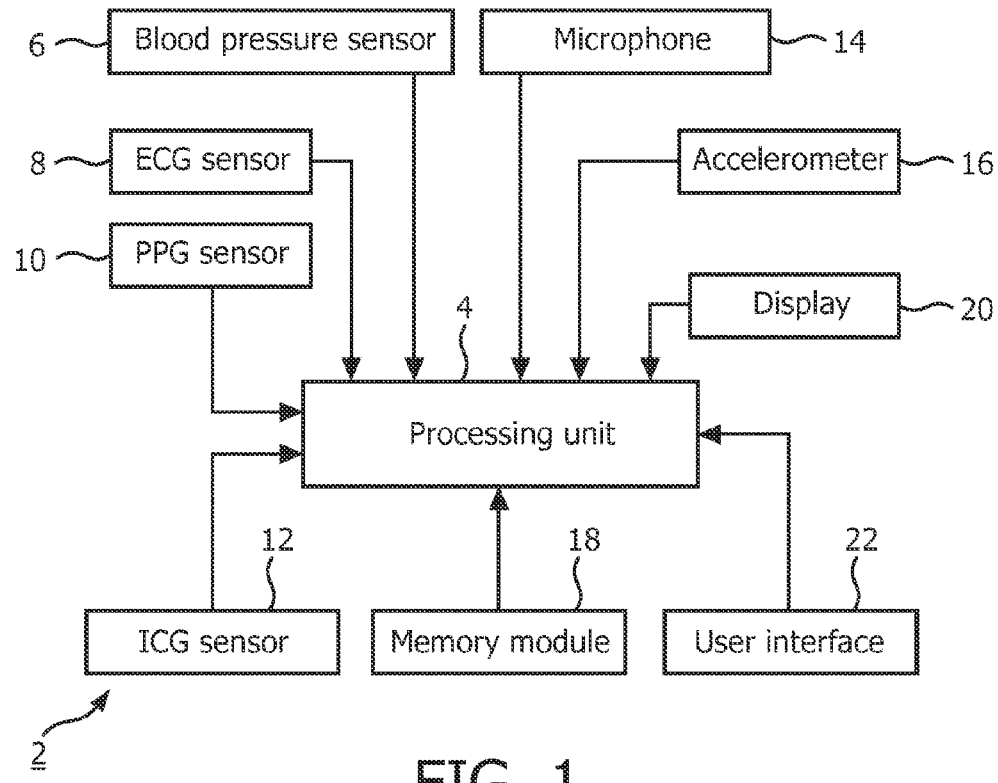
FIG. 1 is diagram illustrating the input signals to a processing unit according to a particular embodiment of the invention and the cardiovascular system parameters that can be derived.

FIG. 1 shows an apparatus 2 according to an embodiment of the invention, which is based on a multi-signal approach using input signals that a) can be monitored non-invasively by a patient reliably in a home environment, and b) are closely linked to the cardiovascular status of the patient. In preferred embodiments of the invention, the following signals are acquired and provided to a processing unit 4 for analysis: an electrocardiogram (ECG), heart sounds (HS), an impedance cardiogram (ICG) and a photo-plethysmogram (PPG), along with measurements of the systolic and diastolic blood pressure using, for example, a conventional cuff-based blood pressure monitor. These signals provide complementary as well as redundant information on the heart pumping function and the vascular status.

From the signals obtained using these sensors, the processing unit 4 can estimate Systolic Time Intervals (STI), thoracic fluid status and thoracic impedance, as well as vascular status parameters such as pulse transit time (PTT) and pulse arrival time (PAT).

Systolic time intervals (STI) have been shown to be valuable non-invasive measures to assess the performance of the left ventricle of the heart. STI reflects the duration of total electro-mechanical systole, and presents two major components: the pre-ejection period (PEP) and the left ventricular ejection time (LVET). PEP is the time interval between the start of ventricular depolarization and the moment of aortic valve opening, whereas the LVET is defined as the time interval of the left ventricular ejection, which occurs between the opening of the aortic valve and its subsequent closure. PEP is an index of the left ventricular function and indicates changes in myocardial contractility, pre- and after load. The left ventricular ejection period (LVET) can also be related to contractility and to cardiac output.

Vascular status, for example, blood vessel stiffness, can be inferred using pulse wave methodology. One implementation of this method analyses a synchronously measured ECG and PPG from which pulse propagation characteristics of the arterial tree like the PAT can be derived. PAT is defined as time interval between the peak of the R wave of the electrocardiogram signal and the onset of a peripheral photo-plethysmographic pulse, which have been intensively investigated as surrogate measures of blood pressure and vessel stiffness (BP). Since PAT is the sum of PEP and PTT, PTT can be calculated from PAT, if PEP is known.

Figure 2:
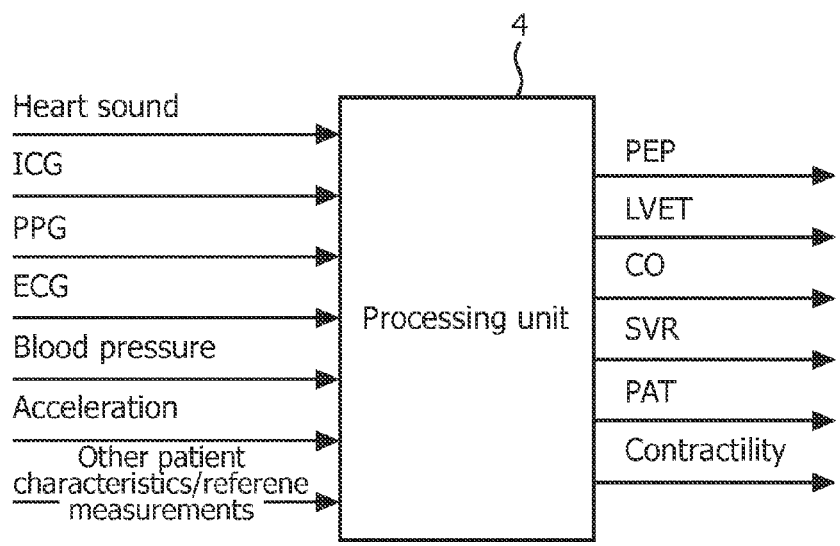
FIG. 2 is a block diagram of an apparatus for use in monitoring the cardiac output of a patient in a home environment according to an embodiment of the invention.

FIG. 2 shows a block diagram of an apparatus 2 according to an embodiment of the invention for allowing a patient to measure their cardiac output, CO, or changes in their CO, in a home environment. As described above, the apparatus 2 preferably comprises a number of different types of sensors that collect the measurements necessary to calculate the CO using the techniques according to the invention. These measurements are provided to a processing unit 4 that processes the measurements and determines the CO, and optionally other parameters related to the health of the cardiovascular system of the patient, such as the systemic vascular resistance (SVR) and/or stroke volume (SV).

Preferably, to enable the apparatus 2 to be used easily and reliably by a patient at home, the apparatus 2 is integrated into an item of clothing in such a way that the various sensors are in the correct positions on the patient's body when the item of clothing is being worn.

According to the techniques for determining CO according to the invention described below, the minimum measurements required to determine CO, or changes in CO, are the systolic blood pressure S, the diastolic blood pressure D and the heart rate of the patient. Thus, the apparatus 2 comprises a blood pressure monitor or sensor 6 connected to the processing unit 4 that measures the systolic blood pressure S and the diastolic blood pressure D of the patient. The blood pressure sensor 6 may be in the form of a cuff. The blood pressure sensor 6 may also have an integrated heart rate sensor for measuring the heart rate of the patient, or it may be possible for the processing unit 4 to determine the heart rate of the patient from the signals from the blood pressure sensor 6.

As it is preferable for the apparatus 2 to measure other physiological characteristics of the patient, since these measurements can be used in the determination of the CO, or as surrogate measures to CO to improve the assessment of the health of the patient, the apparatus 2 shown in FIG. 2 further comprises an electrocardiogram (ECG) sensor 8, a photoplethysmogram (PPG) sensor 10, an impedance cardiogram (ICG) sensor 12, one or more microphones 14 and an accelerometer 16. The microphone or microphones 14 are to be located on the chest wall on the patient in the region of the heart (for example at the left sternum border and at the apex position) to measure the sound of the mechanical activity of the patient's heart. The signal from the accelerometer 16 is used to determine if the patient is in the correct posture (through detection of the direction of gravity), since the posture of the patient can affect the measurements of various physiological characteristics, such as the pre-ejection period (PEP), as described in more detail below. The sensors used in the apparatus 2 according to the invention are individually known in the art, and will not be described in detail herein.

It will be appreciated that although FIG. 2 shows, for example, an ECG sensor 8 and PPG sensor 10, in preferred embodiments of the invention these 'sensors' may merely comprise the electronic components necessary to extract or measure the relevant information from the patient's body (e.g. a number of skin electrodes in the case of the ECG sensor 8 and a light source and light sensor in the case of the PPG sensor 10), with the processing unit 4 being configured to interpret and analyze the signals from the components in order to determine the ECG and PPG measurements. Configuring the sensors and processing unit 4 in this way allows the overall size and cost of the apparatus 2 to be minimized, since it is not necessary to include separate processing units for each of the different types of sensor.

The apparatus 2 further comprises a memory module 18 for storing, for example, the measurements from the sensors prior to, during and/or after their processing by the processing unit 4, the results of the estimation of the cardiac output and other physiological characteristics, any other parameters or patient characteristics that are required during the processing of the sensor measurements (for example the weight and height of the patient, patient-specific calibration factors and/or reference measurements of the cardiac output or other parameters obtained in a clinical environment).

The apparatus 2 also comprises a display 20 that can be used to display the results of the CO or other parameter estimation to the patient, or instructions regarding the operation and status of the apparatus 2. Finally, the apparatus 2 comprises a user interface 22, such as a button, keypad, keyboard or other touch-sensitive input device, for allowing the patient to control the operation of the apparatus 2.

Three different equations for estimating the cardiac output (or changes in the cardiac output) according to the invention are described in more detail below.

The cardiovascular system can be modeled by an RC network. In the simplest model, the heart is represented as a current source and systemic circulation as a resistor. Given mean arterial pressure (MAP) and systemic vascular resistance (SVR), CO may be computed via Ohm's law as follows:

$$CO = MAP/SVR \qquad (1)$$

A more complex model takes into account the capability of arteries to store blood, which is represented by a capacitance C. Here, CO is given by:

$$CO = HR*SV \qquad (2)$$

where SV is stroke volume, and $$CO \alpha HR*C(S-D) \quad (3)$$

where S is systolic blood pressure and D is diastolic blood pressure, which can easily be measured using a cuff-based blood pressure monitor 6. However, it is difficult to provide a reliable estimate of C and to find a patient-specific calibration factor K (where K is given by CO=K*(S−D)).

An approach proposed by Liljestrand (G Liljestrand and E Zander. Vergleichende Bestimmungen des Minutenvolumens des Herzens beim Menschen mittels der tickoxydulmethode and durch Blutdruckmessung. Z Ges Exp Med, 59:105-122, 1928) is to infer C as $$C \alpha 1/(S+D) \quad (4)$$

which gives, after calibration with K via a reference measurement of CO (i.e. K=$CO_{ref}$/(S−D)), a good estimate of CO.

However, in home monitoring scenarios, such as that envisaged for the present invention, it is not strictly necessary to determine an absolute value for cardiac output, and determining relative changes in cardiac output can be sufficient.

Therefore, in a first implementation of the invention, the processing unit 4 can evaluate the relative change in cardiac output using:

$$\frac{CO}{CO_{ref}} = \left(HR \frac{S-D}{S+D}\right) \Big/ \left(HR \frac{S-D}{S+D}\right)_{ref} \quad (5)$$

where $(\ldots)_{ref}$ is obtained from an earlier measurement of the cardiac output. This earlier measurement can be an earlier measurement obtained using the apparatus 2 according to the invention, or measurements of HR, S and D obtained in a clinical environment using state-of-the-art techniques. The reference measurements or patient-specific calibration factor can be stored in the memory module 18.

Thus, this approach allows the apparatus 2 to track relative changes in cardiac output compared to a reference measurement e.g. taken at the hospital before discharge or during nurse visits at the patient's home.

In a second implementation of the invention, the processing unit 4 can estimate the absolute cardiac output. In this implementation, the patient-specific calibration factor K needs to be determined from a reference measurement of the cardiac output.

$$CO = CO_{ref}\left(HR \frac{S-D}{S+D}\right) \Big/ \left(HR \frac{S-D}{S+D}\right)_{ref} \quad (6)$$

Figure 3:
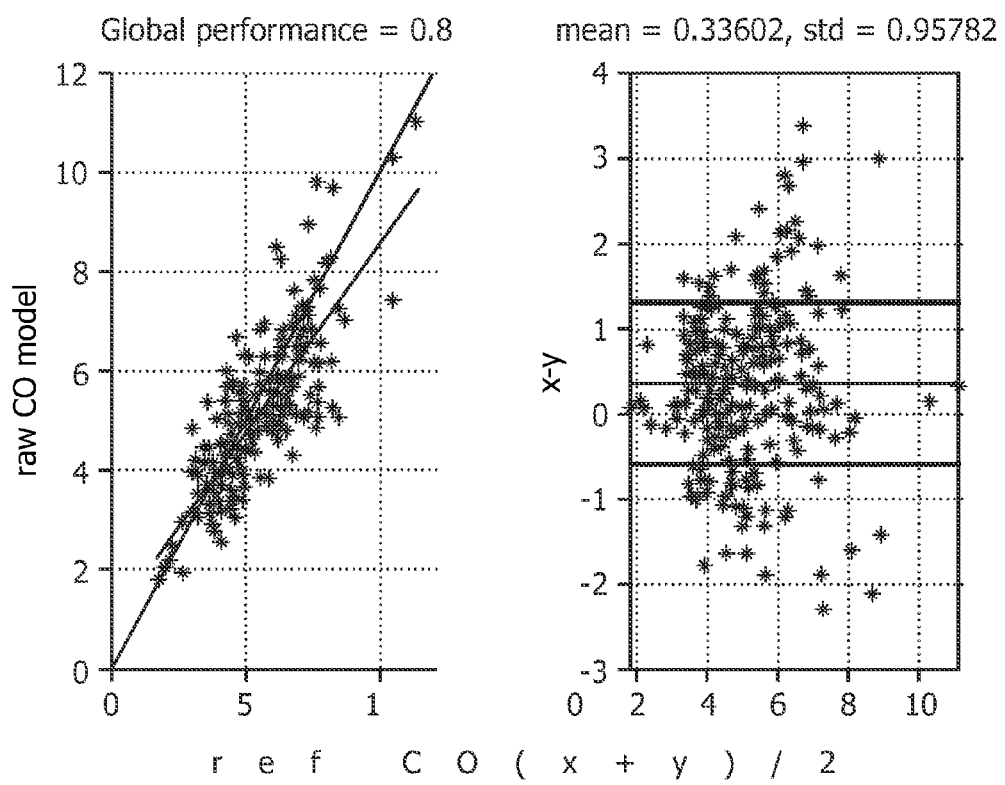
FIG. 3 is a graph illustrating the effectiveness of a technique for calculating cardiac output according to the invention compared to a reference cardiac output measurement technique.

FIG. 3 illustrates the performance of calibrated CO measurements obtained using equation (6) (labeled the 'raw CO model' in FIG. 3) vs. reference measurements obtained using thermodilution (labeled ref 'CO' in FIG. 3). The factor K is determined from a reference CO measurement. The left hand graph shows a 45° plot and the right-hand graph is a Bland-Altman plot, which is used to compare with measures obtained by different measurement methods.

In a third implementation of the invention, relative changes in cardiac output are tracked by estimating the capacitance/compliance C via measurements of the Pulse Transit Time (PTT).

As described in "Non-Invasive Cuff-less Measurements of the Arterial Blood Pressure: What does Pulse Transit Time tell us all about?" by Aubert et al., Proc. ESGCO'06, pp. 211-214, Jena, Germany, May 2006, the compliance C is related to the Pulse Transit Time (PTT) via:

$$C \alpha PTT^2 \quad (7)$$

Using the apparatus 2 shown in FIG. 2, PTT can be measured based on time differences of features in synchronously acquired ECG, heart sound, ICG and peripheral PPG measurements. Since $$PAT=PEP+PTT \quad (8)$$

PTT can be calculated from:

$$PTT=PAT-PEP \quad (9)$$

PAT is defined as the time interval between the peak of the R wave of the electrocardiogram and the onset of a peripheral photo-plethysmograph, where both signals are acquired by the apparatus 2 described above.

PEP can be estimated using the signals obtained by the apparatus 2 in one or more ways. Firstly, PEP can be inferred from simultaneously acquired ECG and heart sounds, as described in "Comparison of Systolic Time Interval Measurement Modalities for Portable Devices" by P. Carvalho et. al., EMBC-2010, 32nd Annual Int. Conf. of the IEEE Engineering in Medicine and Biology Society, 606-609, 2010. Alternatively, PEP can be derived from an ECG and ICG as described in "Robust Characteristic Points for ICG: Definition and Comparative Analysis" by P. Carvalho et. al., Biosignals, Int. Conf. on Bio-Inspired Systems and Signal Processing, 2011.

Figure 4:
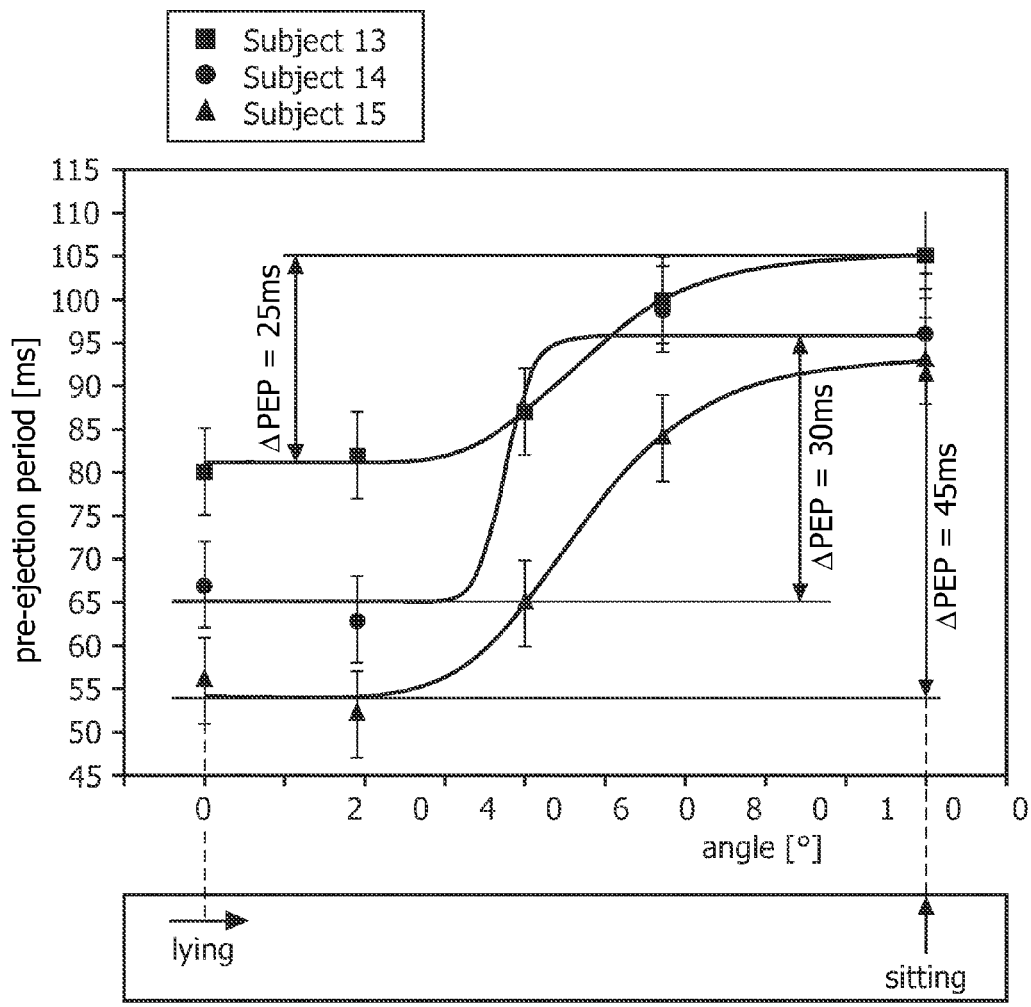
FIG. 4 is a graph illustrating the importance of the patient being in the correct posture when measuring the pre-ejection period.

Reliable measurements of systolic time intervals, for example PEP, require the patient to be in the same orientation with respect to gravity each time the measurement is taken. An example of the effect of body posture on PEP estimation is shown in FIG. 4 and described in "Continuous Cuff-less Blood Pressure Monitoring based on the Pulse Arrival Time Approach: the Impact of Posture" by Muehlsteff J., Aubert X. and Morren G., Proc. IEEE EMBC 2008, Vancouver, Canada, pp. 1691-1694, 20-24 Aug. 2008. Thus, it can be seen that the measured pre-ejection period is longer when a patient is sitting upright than when lying down. It does not matter which posture the patient is in when PEP is measured, however it is required that the patient is in the same posture each time when PEP is measured.

Thus, in embodiments of the invention in which PEP is to be measured, the signal from the accelerometer 16 is processed to determine the orientation of the patient thorax (or any other part of the upper body of the patient to which the accelerometer 16 is attached) during a measurement of PEP. If the measurement positions of the measurements of interest (i.e. a reference measurement and follow-up measurements) are not comparable, then a feedback system can guide the patient to adjust their body into the correct posture.

Using equation (3) with equation (7) gives:

$$CO \alpha HR(S-D)PTT^2 \quad (10)$$

Alternatively, using equation (3) with equations (7) and (9) gives:

$$CO \alpha HR(S-D)(PAT-PEP)^2 \quad (11)$$

If it is only necessary to monitor changes in the cardiac output of the patient, then relative CO is given by:

$$\frac{CO}{CO_{ref}} = (HR(S-D)(PAT-PEP)^2)/(HR(S-D)(PAT-PEP)^2)_{ref} \quad (12)$$

From equation (3), it can be seen that if stroke volume (SV) is to be estimated for a patient, then similar concepts to the three implementations described above can be used, since $$SV \alpha C(S-D) \quad (13)$$

In this case, heart rate is not taken into account.

If an estimate of the systemic vascular resistance (SVR) is to be derived, then equation (1) gives:

$$SVR = MAP/CO \quad (14)$$

where MAP is the mean arterial blood pressure, which is related to S and D as follows:

$$MAP = S/3 + 2D/3 \quad (15)$$

Relative changes of SVR are therefore given via equation (14) as:

$$\left(\frac{SVR}{SVR_{ref}}\right) = \left(\frac{MAP}{MAP_{ref}}\right)\left(\frac{CO_{ref}}{CO}\right) \quad (16)$$

Since MAP can be easily derived from the measured S and D, and as ($CO_{ref}/CO$) is given by equation (12) or (5), relative changes of SVR can be monitored.

It will be appreciated that in order to improve the inference of CO, SV and SVR as well as to personalize critical thresholds, patient characteristics like age, sex, body mass index (BMI), weight, as well as the patient health history can also be taken into account.

Figure 5:
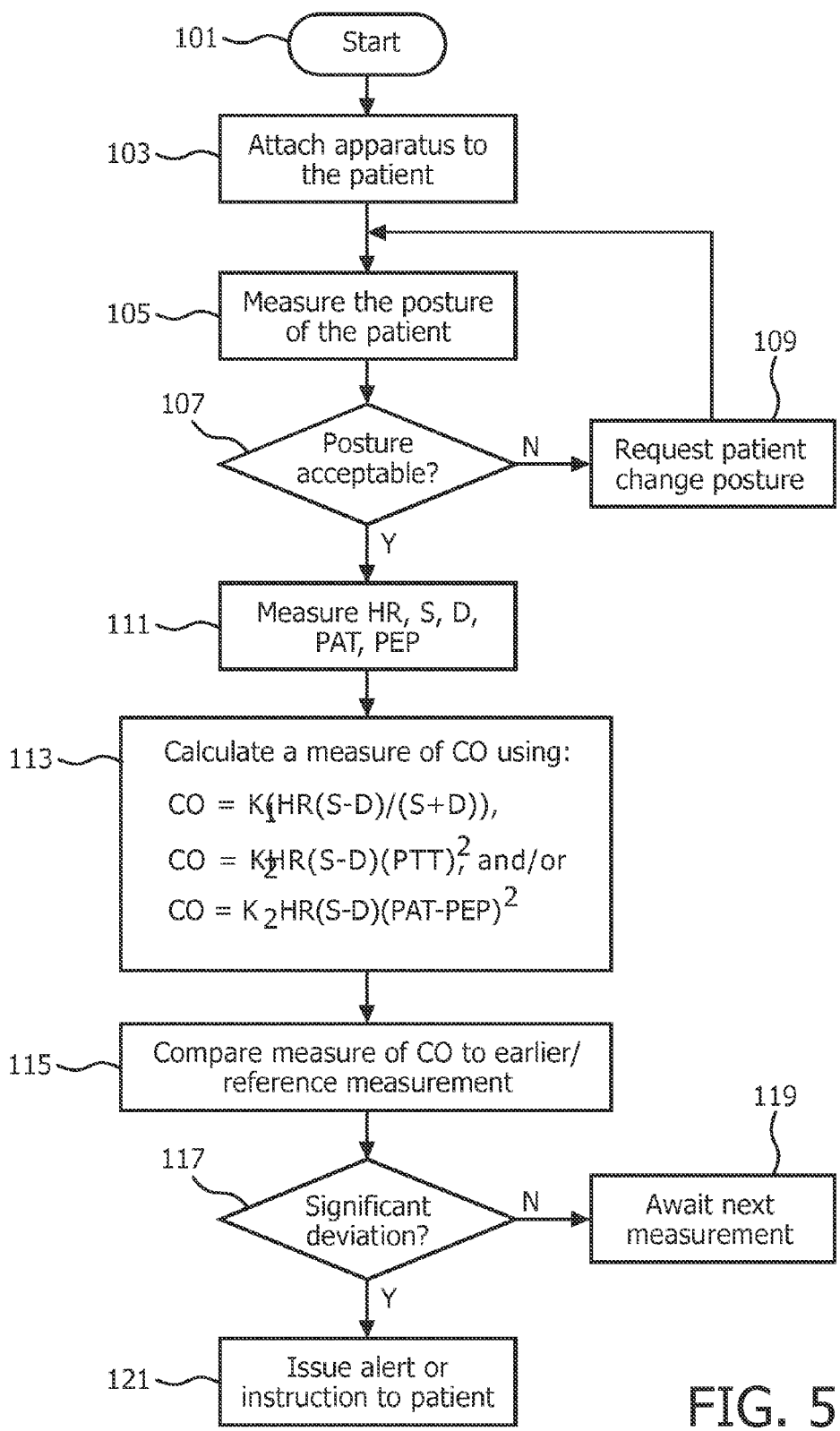
FIG. 5 is a flow chart of a method according to an embodiment of the invention.

An exemplary method according to an embodiment of the invention for measuring cardiac output is shown in FIG. 5. The method starts at step 101. In step 103, the patient attaches the apparatus 2 to themselves. This step can comprise putting on the item of clothing into which the apparatus 2 is integrated, and/or attaching the appropriate sensor(s) to the correct parts of the patient's body (e.g. blood pressure cuff on their arm, ECG electrodes on their chest, etc).

Although not shown in FIG. 5, the apparatus 2 can execute a diagnostic routine after the patient has put on the apparatus 2 to check that the sensors are able to obtain the required measurements. If it is found that any sensor cannot obtain the required measurement, then the patient can be alerted that there is a problem through display 20. The display 20 may also provide instructions for the patient to follow in order to make sure that the sensors are positioned correctly on their body and correctly attached.

Once the apparatus 2 is attached to the patient, the apparatus 2 determines the posture or orientation of the patient using the measurements from the accelerometer 16 (step 105). Techniques for determining the orientation or posture of a patient from accelerometer measurements are well-known in the art and will not be described further herein.

If it is found in step 107 that the posture or orientation of the patient is not acceptable (i.e. the patient is not in the same or sufficiently close orientation or posture as a previous cardiac output measurement or reference measurement), then the apparatus 2 can issue an instruction or error to the patient via display 20 to indicate the patient needs to correct or change their posture (step 109). The method then returns to step 105 (perhaps after a short delay to allow the patient to change their posture) and the posture of the patient is checked again.

If it is found in step 107 that the posture or orientation of the patient is acceptable (i.e. the patient is in the same or sufficiently close orientation or posture as a previous cardiac output measurement or reference measurement), then the apparatus 2 proceeds to obtain measurements of (in some embodiments) heart rate, systolic blood pressure, diastolic blood pressure, pulse arrival time and the pre-ejection period (step 111). As described above, some of these parameters can be measured directly (e.g. heart rate, systolic blood pressure and diastolic blood pressure), whereas others can be derived from the measurements by the sensors in the apparatus 2.

Then, in step 113, the processing unit 4 in the apparatus 2 calculates the cardiac output, or a measure of the change in cardiac output, since a previous or reference measurement. The processing unit 4 calculates the CO or change in CO using one or both of the relationships below $$CO = K_1\left(HR\frac{S-D}{S+D}\right) \quad (17)$$

$$CO = K_2 HR(S-D)(PTT)^2 \quad (18)$$

$$CO = K_2 HR(S-D)(PAT-PEP)^2 \quad (19)$$

where $K_1$ and $K_2$ are patient-specific calibration factors. Of course, where relative values of CO are determined, it is not necessary to know or derive values for $K_1$ or $K_2$.

In step 115, the processing unit 4 compares the measure of CO with an earlier measurement to determine the change in the health of the patient. It will be appreciated that where the processing unit 4 calculates a relative value for CO, that this step can be omitted.

If it is found in step 117 that there is no significant deviation from the earlier measurement then the apparatus 2 waits until it is time to make the next calculation of CO (step 119). A significant deviation can be of the order of a change of at least 15% from the previous measurement.

A typical value for CO is in the range of 4-8 liters/minute. Patients with heart failure have a reduced CO (typically less than 4 l/min). Thus, a deviation of the order of 15% means that a change in the CO of around 0.6 l/min will be considered significant. It will be appreciated that a threshold value (or upper and lower bounds) can be set for determining whether a deviation is significant, and this value or bounds can be set at a predetermined value for a group of patients with a specific medical condition (e.g. heart failure) or it can be set at a value specific to that patient depending on the healthcare professional's assessment of the patient's current condition.

If it is found in step 117 that there is a significant deviation from the earlier measurement, then the processing unit 4 can issue an alert or instruction to the patient (step 121) via the display 20. This alert or instruction can, for example, advise the patient to seek immediate medical assistance, to adjust their medication regimen or to confirm the measurement by taking a further one.

It will be appreciated that although the invention is described as being intended for monitoring patients with congestive heart failure, the apparatus 2 and method according to the invention can be used in the management of any other chronic health condition, in which measurements of the cardiovascular system provide useful indications of the patient's condition. It will also be appreciated that the invention can be used in sport applications to monitor the effect of training on the capacity and efficiency of the cardiovascular system.

It is therefore desirable to provide ways to easily and reliably determine cardiac output and the other measures indicated above for a patient in unsupervised settings, such as at home, for use in monitoring the health of the cardiovascular system of the patient and adapting the dosage or type of medication prescribed to the patient to improve the management of CHF and reduce side effects of the medication.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining a measure of the cardiac output, CO, of a patient with a monitoring apparatus, the monitoring apparatus comprising a hardware processing unit and one or more physiological sensors, the method comprising:
obtaining, with the processing unit, measurements of one or more physiological characteristics of the patient from the one or more physiological sensors, the physiological characteristics including at least the heart rate, HR, of the patient, the systolic blood pressure, S, of the patient and the diastolic blood pressure, D, of the patient; and
processing, with the processing unit, the measurements to determine a measure of the cardiac output of the patient;
wherein the measure of the cardiac output of the patient is derived using the relationship:

$$CO = K_1\left(HR\frac{S-D}{S+D}\right),$$

$$CO = K_2 HR(S-D)(PTT)^2,$$

and/or $$CO = K_2 HR(S-D)(PAT-PEP)^2,$$

where $K_1$ and $K_2$ are patient-specific calibration factors, PAT is the pulse arrival time, PEP is the pre-ejection period and PTT is the pulse transit time, the time taken for a pulse wave to travel between two points in the body of the patient.

2. A method as claimed in claim 1, wherein $K_1$ and/or $K_2$ are determined by the processing unit from a reference measurement of the cardiac output of the patient.

3. A method as claimed in claim 1, wherein the measure of the cardiac output of the patient is a measure of the change in the cardiac output from an earlier cardiac output measurement or a reference measurement for cardiac output, and the measure of the change in the cardiac output is given by $$\frac{CO}{CO_{ref}} = \left(HR\frac{S-D}{S+D}\right) \Big/ \left(HR\frac{S-D}{S+D}\right)_{ref},$$

$$\frac{CO}{CO_{ref}} = (HR(S-D)PTT^2)/(HR(S-D)PTT^2)_{ref},$$

and/or $$\frac{CO}{CO_{ref}} = (HR(S-D)(PAT-PEP)^2)/(HR(S-D)(PAT-PEP)^2)_{ref}$$

where $(\ldots)_{ref}$ denotes the earlier cardiac output measurement or the reference measurement for cardiac output.

4. A method as claimed in claim 1, wherein the step of obtaining measurements comprises obtaining, from the one or more physiological sensors, an electrocardiogram signal, a photoplethysmogram signal, and at least one of heart sounds and an impedance cardiogram signal; and wherein the step of processing comprises processing the electrocardiogram signal and photoplethysmogram signal to determine the pulse arrival time, and processing the at least one of the heart sounds or the impedance cardiogram signal and the electrocardiogram signal to determine the pre-ejection period.

5. A method as claimed in claim 1, further comprising the steps of:
comparing, with the processing unit, the measure of the cardiac output of the patient or measure of the change in the cardiac output of the patient to one or more threshold values; and
providing, with the processing unit, an output indicating the result of the step of comparing.

6. A method as claimed in claim 1, the method further comprising the steps of:
obtaining, with the processing unit, measurements of acceleration acting on the patient during the measurement of the physiological characteristics of the patient;
processing, with the processing unit, the measurements of acceleration to determine the posture of the patient;
comparing, with the processing unit, the determined posture of the patient to a predetermined posture for the patient; and
providing, with the processing unit, feedback to the patient regarding their posture if the determined posture is not the same or sufficiently close to the predetermined posture.

7. A method as claimed in claim 6, wherein the predetermined posture corresponds to the posture of the patient during a previous set of measurements of the physiological characteristics of the patient.

8. A method as claimed in claim 1, further comprising the step of:
processing, with the processing unit, the measurements to determine a measure of the systemic vascular resistance, SVR, of the patient from the measure of the cardiac output of the patient using the relationship:

SVR=MAP/CO where MAP is the mean arterial blood pressure and is given by:

MAP=$S$/3+2$D$/3.

9. An apparatus for use in monitoring the cardiac output, CO, of a patient, the apparatus comprising:
a hardware processing unit configured to:
receive measurements of one or more physiological characteristics of the patient from one or more physiological sensors, the physiological characteristics including at least the heart rate, HR, of the patient, the systolic blood pressure, S, of the patient and the diastolic blood pressure, D, of the patient; and
process the measurements to determine a measure of the cardiac output of the patient;
wherein the measure of the cardiac output of the patient is derived using the relationship:

$$CO = K_1\left(HR\frac{S-D}{S+D}\right),$$

$$CO = K_2 HR(S-D)(PTT)^2,$$

and/or $$CO = K_2 HR(S-D)(PAT-PEP)^2$$

where $K_1$ and $K_2$ are patient-specific calibration factors, PAT is the pulse arrival time, PEP is the pre-ejection period and PTT is the pulse transit time, the time taken for a pulse wave to travel between two points in the body of the patient.

10. An apparatus as claimed in claim 9, wherein the measure of the cardiac output of the patient determined by the processing unit is a measure of the change in the cardiac output from an earlier cardiac output measurement or a reference measurement for cardiac output, and the processing unit is configured to process the measurements to determine the measure of the change in the cardiac output using:

$$\frac{CO}{CO_{ref}} = \left(HR\frac{S-D}{S+D}\right) \bigg/ \left(HR\frac{S-D}{S+D}\right)_{ref},$$

$$\frac{CO}{CO_{ref}} = (HR(S-D)PTT^2)/(HR(S-D)PTT^2)_{ref},$$

and/or $$\frac{CO}{CO_{ref}} = (HR(S-D)(PAT-PEP)^2)/(HR(S-D)(PAT-PEP)^2)_{ref}$$

where $(\ldots)_{ref}$ denotes the earlier cardiac output measurement or the reference measurement for cardiac output.

11. An apparatus as claimed in claim 9, wherein the processing unit is further configured to:
 compare the measure of the cardiac output of the patient or measure of the change in the cardiac output of the patient to one or more threshold values; and
 provide an output indicating the result of the comparison.

12. An apparatus as claimed in claim 9, further comprising the one or more physiological sensors, the one or more physiological sensors including: a blood pressure monitor, a heart rate sensor, an electrocardiogram sensor, a photoplethysmogram sensor, an impedance cardiogram sensor and one or more microphones.

13. An apparatus as claimed in claim 12, wherein the one or more physiological sensors are integrated into an item of clothing to be worn by the patient.

14. An apparatus as claimed in claim 9, wherein the processing unit is further configured to receive measurements of the acceleration acting on the patient and to process the measurements of the acceleration to determine the posture of the patient.

* * * * *